US00PP15936P3

(12) United States Plant Patent
Hofmann

(10) Patent No.: US PP15,936 P3
(45) Date of Patent: Aug. 30, 2005

(54) **NEW GUINEA *IMPATIENS* PLANT NAMED 'FISNICS REDGOLD'**

(50) Latin Name: *Impatiens hawkeri*
Varietal Denomination: Fisnics Redgold

(75) Inventor: Birgit C. Hofmann, Bendorf (DE)

(73) Assignee: Florfis AG (CH)

( * ) Notice: Subject to any disclaimer, the term of this patent is extended or adjusted under 35 U.S.C. 154(b) by 22 days.

(21) Appl. No.: 10/829,350

(22) Filed: Apr. 22, 2004

(65) Prior Publication Data

US 2004/0237160 P1 Nov. 25, 2004

(30) Foreign Application Priority Data

Apr. 22, 2003 (CH) ..... 03-1989

(51) Int. Cl.[7] ..... A01H 5/00

(52) U.S. Cl. ..... Plt./318

(58) Field of Search ..... Plt./318

*Primary Examiner*—Kent Bell

(74) *Attorney, Agent, or Firm*—Foley & Lardner, LLP

(57) ABSTRACT

A new and distinct cultivar of New Guinea *Impatiens* plant named 'Fisnics Redgold' particularly characterized by the combined features of red to cherry red flower color; large to very large flowers with distinctly lobed petals; deep green, glossy foliage with yellow variegation, not always visible; medium sized or larger growth habit, v-shaped, moderately dense; and medium to moderately late flowering response.

1 Drawing Sheet

Genus and species of the plant claimed: *Impatiens hawkeri.*

Variety denomination: 'Fisnics Redgold'.

BACKGROUND OF THE INVENTION

The present invention comprises a new and distinct cultivar of New Guinea *Impatiens,* botanically known as *Impatiens hawkeri*, and hereinafter referred to by the cultivar name 'Fisnics Redgold'.

'Fisnics Redgold' is a product of a planned breeding program and originated from a hybridization made by the inventor, Birgit C. Hofmann, in a controlled breeding program in Hillscheid, Germany, in 2000.

The female parent was the commercial variety 'Celebration Light Salmon' (U.S. Plant Pat. No. 12,087 under the denomination 'Balcelisow'), characterized by light salmon colored flowers with white centers, deep green foliage with sometimes yellow variegation visible along the midrib, and with about medium sized plant habit.

The male parent was a proprietary seedling designated no. 98-4128-1 (unpatented), having very large, purple flowers, dark green leaves with red veins, and small to medium sized plant habit.

'Fisnics Redgold' was discovered and selected as one flowering plant within the progeny of the stated cross by the inventor in April 2001 in a greenhouse in Galdar, Canary Islands, Spain.

The first act of vegetative or asexual reproduction of 'Fisnics Redgold' was accomplished when cuttings were taken from the initial selection in July 2001 in a controlled environment in Galdar, Gran Canaria, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisnics Redgold' are firmly fixed and are retained through successive generations of asexual reproduction. The new cultivar reproduces true to type.

'Fisnics Redgold' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany under greenhouse conditions which approximate those generally used in commercial practice.

BRIEF SUMMARY OF THE INVENTION

The following traits have been repeatedly observed and are determined to be basic characteristics of 'Fisnics Redgold', which in combination distinguish this *impatiens* as a new and distinct cultivar:

1. Red to cherry red flower color;
2. Large to very large flowers with distinctly lobed petals;
3. Deep green, glossy foliage with yellow variegation, not always visible;
4. Medium sized or larger growth habit, v-shaped, moderately dense; and
5. Medium to moderately late flowering response.

Of the many commercial cultivars known to the inventor, the most similar in comparison to 'Fisnics Redgold' is the variety 'Kiotoa' commercially known as 'Painted Paradise Red' (unpatented).

In comparison to 'Kiotoa', 'Fisnics Red' has larger flowers of a more bluish-red hue, weaker and less often developing variegation of leaves, and more vigorous and less tight growth characteristics.

BRIEF DESCRIPTION OF THE DRAWING

The accompanying photographic drawing shows typical flower and foliage characteristics of 'Fisnics Redgold' with colors being as true as possible with illustrations of this type. The photographic drawing shows a side view of a typical flowering plant of 'Fisnics Redgold'.

DETAILED BOTANICAL DESCRIPTION

In the following description color references are made to The Royal Horticultural Society Colour Chart (R.H.S.). The color values were determined indoors from plants grown in Hillscheid, Federal Republic of Germany, under greenhouse conditions which approximate those generally used in commercial practice.

The description is based on plants which were planted as rooted cuttings in 12 cm pots in late February 2003, and then grown in the greenhouse at 16° C. minimum temperature. Most observations and measurements were made after the beginning of flowering in mid May, when the plants were about 12 weeks old.

PLANT

General appearance and form:

*Plant habit.*—Medium or larger in size, initially tight, later only moderately tight structure, with upright slanting branches (v-shaped), freely branching; growth is indeterminate, though weak after beginning of flowering.

*Height.*—15.3 cm.

*Width.*—29.7 cm.

*Number of branches.*—14–16.

*Length of branches.*—9–11 cm.

*Internode length.*—3.0–4.0 cm.

*Diameter of branches.*—6–7 mm.

*Stem color.*—Brownish, from RHS 181 A to RHS 183 C.

*Propagation.*—Terminal tips for cuttings.

*Rooting.*—Roots initiate in about 18 days at 22° C., from sticking to transplanting.

*Cultivation time.*—It takes about 10–11 weeks of growing time to produce a marketable flowering plant in a 12 cm container.

Foliage:

*Leaf arrangement.*—Primarily in whorls.

*Shape of leaf.*—Elliptic, relatively large, with acute base and acuminate tip.

*Surface.*—Glossy and smooth.

*Margin.*—Slightly serrated, fine ciliation.

*Leaf length.*—13.0 cm on average.

*Leaf width.*—4.5–4.75 cm.

*Upper surface color.*—Deep medium green, with weak variegation, mature leaves between RHS 137 A and RHS 139 A young leaves RHS 137 A.

*Variegation.*—Relatively weak, usually developed during the summer months, but not at lower light intensity in spring or fall: a greenish-yellow stripe along the midrib, color RHS 150 A.

*Veins on upper surface.*—Pale light green, RHS 145 C.

*Lower surface color.*—Light green, RHS 139 C (both young and mature leaves).

*Veins on lower surface.*—RHS 181 D.

*Petiole size.*—10–20 mm in length, 2.5–3 mm in diameter.

*Petiole color.*—Upper side dark-red, RHS 184 D, lower side RHS 181 D.

INFLORESCENCE

Flowering response: About 10 weeks after planting of rooted cuttings.

Flowering season: Generally indeterminate, mainly from March to October, depending on light intensity.

Flower:

*Number of flowers per node.*—6–8, in various stages of development.

*Form of corolla.*—Single, 5 petals.

*Corolla shape.*—Nearly round, with the petals overlapping, mostly flat.

*Corolla size.*—Average length: 80 mm. Average width: 78 mm. Depth of corolla: 10 mm.

*Shape of petals.*—Cordate, relatively deeply lobed at the top end. Top petal: 33 mm long, 53 mm wide. Lateral petals: 38 mm long, 39 mm wide. Lower petals: 40 mm long, 44 mm wide.

*Texture.*—Smooth, velvety.

*Aspect.*—Flat.

*Color (general tonality from a distance of three meters)*.—Cherry red.

*Main color of upper surface.*—A slightly more bluish hue than RHS 46 B to 46 C.

*Eye zone and markings.*—Weak, bluish-pink at the base of the petals RHS 74 B to 74 C, a narrow stripe of the same color may be visible dividing the upper petal.

*Color of lower surface.*—Light red, RHS 50 A.

*Spur color.*—Dark purple-brown, RHS 185 A.

*Spur shape and size.*—Downwardly curved, 62 mm long, 3 mm in diameter at the flower end.

*Peduncle size.*—4.5 cm in length, 2 mm in diameter.

*Peduncle color.*—Brownish pink, RHS 181 D.

*Flower bud.*—Ovoid shape, 25 mm in length, 16 mm in diameter, main color RHS 46 C.

Reproductive organs:

*Stamens.*—5 in number, fused, upper surface color is mainly RHS 46 C.

*Anthers.*—Hooded.

*Pollen.*—Whitish-yellow, about RHS 8 D.

*Style and stigma.*—5 in number, very short, pale yellow, about RHS 150 D.

*Ovary.*—5-celled, 5 mm long, surface color green, RHS 139 B.

Disease/pest resistance/susceptibility: No observations to date.

I claim:

1. A new and distinct cultivar of New Guinea *Impatiens* plant named 'Fisnics Redgold' as described and illustrated herein.

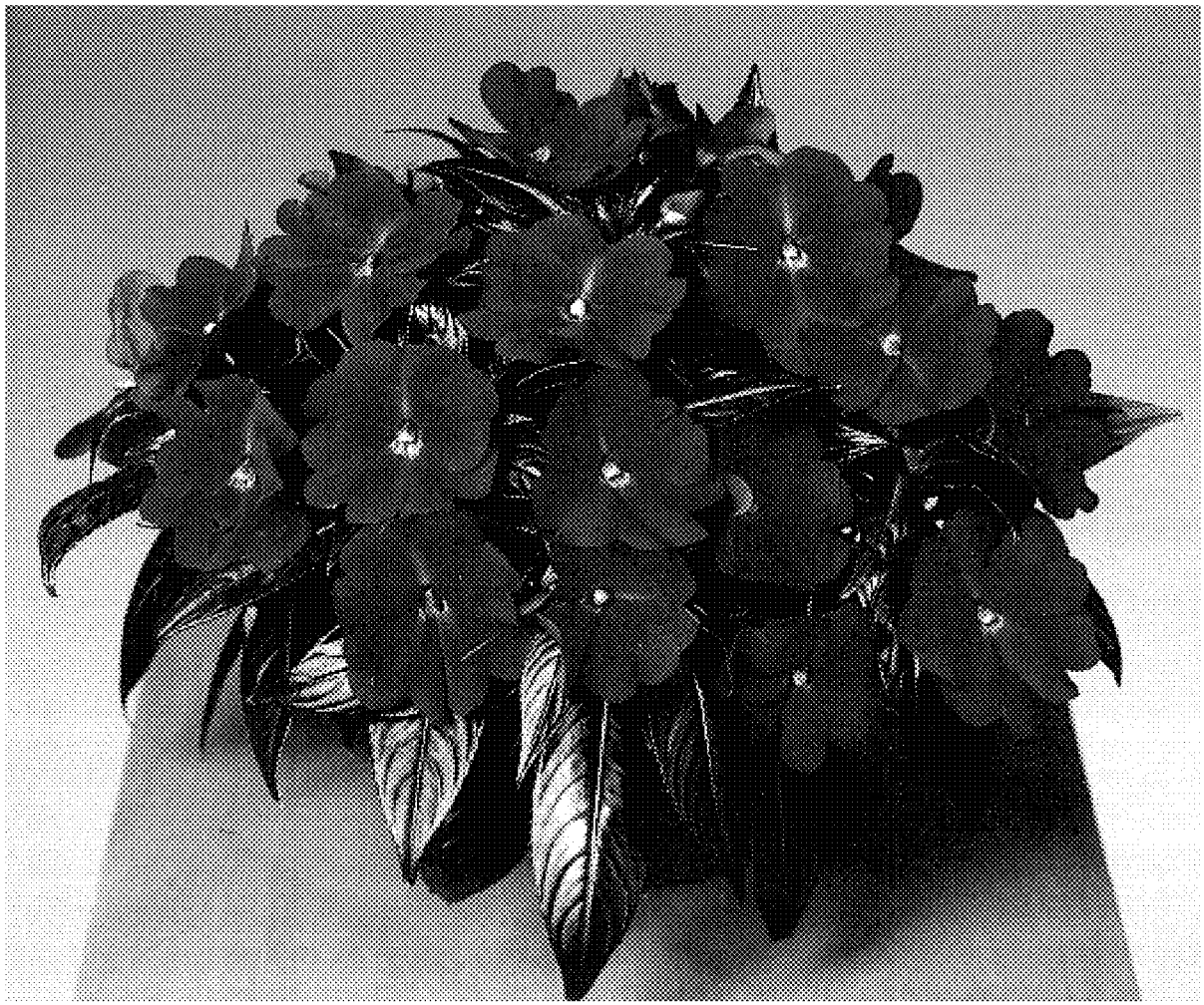

* * * * *